US007737399B1

(12) United States Patent
Carrieri et al.

(10) Patent No.: US 7,737,399 B1
(45) Date of Patent: Jun. 15, 2010

(54) INFRARED MUELLER MATRIX ACQUISITION AND PREPROCESSING SYSTEM AND METHOD

(75) Inventors: Arthur H. Carrieri, Abingdon, MD (US); David J. Owens, Kingsville, MD (US); Jonathan C. Schultz, Perryville, MD (US)

(73) Assignee: The United States of America as represented by the Secretary of the Army, Washington, DC (US)

( * ) Notice: Subject to any disclaimer, the term of this patent is extended or adjusted under 35 U.S.C. 154(b) by 121 days.

(21) Appl. No.: 12/256,936

(22) Filed: Oct. 23, 2008

(51) Int. Cl.
*G01J 5/00* (2006.01)
(52) U.S. Cl. .................................... 250/338.1; 356/364
(58) Field of Classification Search ................. 250/225, 250/229, 338.1; 356/364, 367, 369
See application file for complete search history.

(56) References Cited

U.S. PATENT DOCUMENTS

| | | | | |
|---|---|---|---|---|
| 5,241,179 | A | 8/1993 | Carrieri | |
| 5,659,391 | A | 8/1997 | Carrieri | |
| 6,060,710 | A | 5/2000 | Carrieri et al. | |
| 6,389,408 | B1 | 5/2002 | Carrieri | |
| 6,464,392 | B1 | 10/2002 | Carrieri et al. | |
| 6,731,804 | B1 | 5/2004 | Carrieri et al. | |
| 7,038,789 | B1 * | 5/2006 | Carrieri | 356/491 |
| 7,262,414 | B1 | 8/2007 | Carrieri et al. | |

OTHER PUBLICATIONS

Jones, R., "New Calculus for the Treatment of Optical Systems. VII: Properties of the N-matrices," J. Opt. Soc. Am., vol. 38, No. 8, pp. 671-685, Aug. 1948.

Jackson, J., "Plane electromagnetic waves and wave propagation," in *Classical Electrodynamics*, John Wiley & Sons, Inc., 1975, pp. 273-278.

Thompson, R. et al., "Measurement of polarized light interactions via the Mueller matrix," Appl. Opt., vol. 19, No. 8, pp. 1323-1332, Apr. 15, 1980.

Gorman, Jr., J. et al., "Mueller-matrix measurements in a two-component blue-phase mixture," Phys. Rev. A vol. 31, No. 2, pp. 910-913, Feb. 1985.

Wenyan, Y., "The Mueller scattering matrix of two parallel chiral circular cylinders," Microwave and Opt. Tech. Letters, vol. 11, No. 2, pp. 78-83, Feb. 5, 1996.

(Continued)

*Primary Examiner*—David P Porta
*Assistant Examiner*—Mark R Gaworecki
(74) *Attorney, Agent, or Firm*—Ulysses John Biffoni

(57) ABSTRACT

An analog Mueller matrix data acquisition system (AMMS) acquiring middle-infrared Mueller (M) matrices of backscattering surfaces. The M-elements are measured by means of an active photopolarimetric sensor. The AMMS records nine M-elements simultaneously in groups of four modulo 2 incident continuous-wave $CO_2$ laser beams—one incident beam is tuned to a fundamental molecular absorption cross-section by the aerosol of detection interest (analytic wavelength $\lambda_a$) while the other beam is detuned off that resonance band (reference wavelength $\lambda_r$) and in the closest vicinity to $\lambda_a$. Accordingly, those $\Delta M$ elements exhibiting susceptible behavior to the aerosol analyte, driven on-then-off its molecular vibrational resonance band, cues an identification event thus providing detection decision information. The AMMS is comprised of PEM reference frequency synthesizer, optical power regulation, data digitizer, and computer interface components in an interfaced and integrated framework that governs all operations of M-elements production by the photopolarimetric sensor.

21 Claims, 10 Drawing Sheets

OTHER PUBLICATIONS

Floch, M. et al., "Experimental characterization of immersed targets by polar decomposition of the Mueller matrices," Eur. Phys. J. AP 3, pp. 349-358, May 6, 1998.

Yang, P. et al., "Sensitivity of the backscattering Mueller matrix to particle shape and thermodynamic phase," Appl. Opt., vol. 42, No. 21, pp. 4389-4395, Jul. 20, 2003.

Mackey, J. et al., "A compact dual-crystal modulated birefringence-measurement system for microgravity applications," Meas. Sci. Tech. 10, pp. 946-955 (1999).

Kokhanovsky, A., "Parameterization of the Mueller matrix of oceanic waters," J. Geophys. Res., vol. 108, No. C6, 3175 (four pages), 2003.

Fry, E. et al., "Measurement of the Mueller Matrix for Phytoplankton," Limnol. Oceanogr., 30(6), pp. 1322-1326 (1985).

Jiao, S. et al., "Two-dimensional depth-resolved Mueller matrix of biological tissue measured with double-beam polarization-sensitive optical coherence tomography," Opt. Letters, vol. 27, No. 2, pp. 101-103, Jan. 15, 2002.

Angelsky, O. et al., "Investigation of 2D Mueller matrix structure of biological tissues for pre-clinical diagnostics of their pathological states," J. Phys. D: Appl. Phys., 38, pp. 4227-4235 (2005).

Todorović, M. et al., "Determination of local polarization properties of biological samples in the presence of diattenuation by use of Mueller optical coherence tomography," Optics Letters, vol. 29, No. 20, pp. 2402-2404, Oct. 15, 2004.

Bahar, E., "Mueller matrices for waves reflected and transmitted through chiral materials: waveguide modal solutions and applications," J. Opt. Soc. Am. B, vol. 24, No. 7, pp. 1610-1619, Jul. 2007.

Carrieri, A. et al., "Mid-infrared Polarized Light Scattering: Applications for the Remote Detection of Chemical and Biological Contaminations," Technical Report CRDEC-TR-318 (Chemical Research, Development, and Engineering Center, Aberdeen Proving Ground, MD, Jan. 1992 (abstract only).

Carrieri, A. et al., "Differential absorption Mueller matrix spectroscopy and the infrared detection of crystalline organics," Appl. Opt., vol. 37, No. 27, pp. 6550-6557, Sep. 20, 1998.

Carrieri, A. et al., "Computation, visualization, and animation of infrared Mueller matrix elements by surfaces that are absorbing and randomly rough," Appl. Opt., vol. 32, No. 31, pp. 6264-6269, Nov. 1, 1993.

Carrieri, A. et al., "Photopolarimetric lidar duel-beam switching device and Mueller matrix standoff detection method," J. Appl. Remote Sens., vol. 1, 013502, pp. 1-23, Jan. 19, 2007.

Haugland, S. et al., "Identification of contaminant coatings over rough surfaces using polarized IR scattering," Appl. Opt., vol. 31, No. 19, pp. 3847-3852, Jul. 1, 1992.

Carrieri, A., "Neural network pattern recognition by means of differential absorption Mueller matrix spectroscopy," Appl. Opt., vol. 38, No. 17, pp. 3759-3766, Jun. 10, 1999.

* cited by examiner

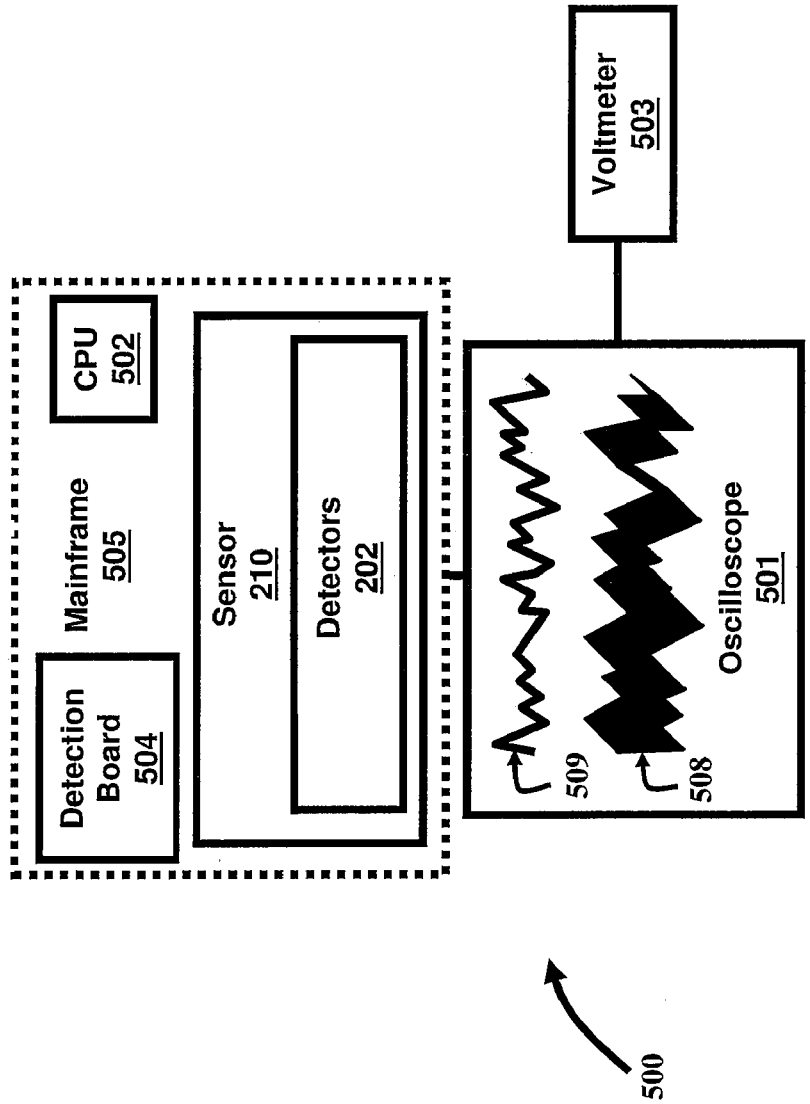
FIG. 5A
FIG. 5B

INFRARED MUELLER MATRIX ACQUISITION AND PREPROCESSING SYSTEM AND METHOD

GOVERNMENT INTEREST

The invention described herein may be manufactured, used, and/or licensed by or for the United States Government.

BACKGROUND

1. Technical Field

The embodiments herein generally relate to an analog electronics system that integrates to a standoff detection sensor for detecting chemical and biological materials at a distance, and, more particularly, to an analog electronics system that measures elements of the Mueller matrix at infrared $CO_2$ laser wavelengths from a photopolarimetric-based sensor apparatus, and preprocesses those data fields so as to identify targeted contaminants—such as biological aerosol and liquid chemical warfare agents or simulants of such compounds—by their unique polarized infrared elastic backscattering signatures brought out in a differential-absorption Mueller matrix spectroscopy (DIAMMS) operation mode of sensor.

2. Description of the Related Art

A variety of systems and methods have been developed and used to detect and identify hazardous chemical and biological threat agents in the field. Passive infrared (PIR) imaging sensors detect airborne chemical threats such as nerve (GA, GB, and GD) and blister (H and L) agents based on the infrared spectrum of the agent. Currently, fielded devices have been reported to detect aerosols at a distance of up to 5 km. Practical PIR detection systems generally have difficulty detecting low levels of chemical-biological warfare (CBW) surface target contaminants because the surfaces are typically at thermal- or pseudo-equilibrium and provide insufficient contrast to identify target contaminants. U.S. Pat. Nos. 5,241,179; 6,464,392; 6,731,804; and 7,262,414, the complete disclosures of which, in their entireties, are herein incorporated by reference, address this issue by externally stimulating the subject target contaminant/background with radiation to produce sufficient contrast when performing detection functions.

Additionally, background radiation and interference encountered in the field can mask the infrared signature of contaminant, making the detection event difficult if not impossible. Uniqueness of detection is, furthermore, a major issue with PIR detection systems as they typically rely on one quantifier; i.e., the infrared signature spectrum.

What is needed in a standoff detection system is technology that provides a truly unique metric for revealing an analytic contaminant (i.e., chemical and biological, or chemical/biological (CB), warfare agents) that can be measured in the field rapidly, reliably, and repeatedly at very low concentration levels of that analyte. The sensor built around this technology must operate remotely at a safe distance in order to detect target contaminants before casualty-producing concentrations are encountered.

SUMMARY

In view of the foregoing, an embodiment herein provides a system for automated acquisition of infrared Mueller (M) matrices of targeted CB aerosols or surface contaminants (analytes) at the backscattering angle. The embodiments herein provide utility to a photopolarimetric-based sensor by (1) facilitating precise delivery of two alternating polarization-modulated infrared laser beams incident onto subject backscatterer, (2) priming its dual photoelastic-modulation (PEM) engine, and (3) establishing optimum backscattering throughput radiance for sequenced acquisition of M-elements. In a standoff identification/detection application of sensor, digitized M-elements of analyte are normalized and filtered into a susceptance class for empirical neural network training. An optimized network model developed from these data performs pattern recognition of the analyte and type-classification of its species.

Another embodiment provides an electronics analog Mueller matrix system (AMMS) comprising an infrared photopolarimetric-based differential-absorption Mueller matrix spectroscopy (DIAMMS) chemical and biological remote sensor comprising a photoelastic-modulation engine and a computer; a reference synthesizing module operatively connected to the remote sensor, the reference synthesizing module comprising circuits generating two primary and six overtone pure coherent sinusoidal frequencies to serve as reference waveforms; a scattergram intensity regulation and control module operatively connected to the reference synthesizing module, the scattergram intensity regulation and control module comprising an electromechanical system that automatically maintains constant magnitude of optical backscattering intensity as the photoelastic-modulation engine permutes to one of a plurality of configurations; a phase correlation module operatively connected to the scattergram intensity regulation and control module, wherein the phase correlation module provides a plurality of Mueller (M) matrix elements as analog signals per fundamental/overtone frequency assignments in scattergram voltage waveforms detected by the remote sensor; a data digitization and computer interface module operatively connected to the phase correlation module, wherein the data digitization and computer interface module digitizes the Mueller matrix analog signals from the phase correlation module and transmits the digitized signals to the computer of the remote sensor; and a graphical user interface (GUI) system operatively connected to the data digitization and computer interface module, wherein the GUI system controls the remote sensor.

Preferably, the reference waveforms are input into junctions of phase-sensitive detection circuits of a succeeding phase correlation module of a second AMMS. Moreover, the plurality of configurations may comprise four configurations. Additionally, the plurality of Mueller (M) matrix elements preferably comprises eight Mueller (M) matrix elements. Furthermore, an output of the plurality of Mueller (M) matrix elements is preferably proportional to a dot product between detected scattergram signals and each reference waveform transmitted by the reference synthesizing module. Preferably, the data digitization and computer interface module comprises a logic control circuit that controls sequences of command and status signals between the data digitization and computer interface module and the scattergram intensity regulation and control module.

The GUI system may comprise automatic control of (i) an optical system of the remote sensor, (ii) safety failsafe operations of the remote sensor, (iii) synchronized acquisition of Mueller matrix elements data, (iv) optimization of data measurements, and (v) preprocessing of acquired data and filtration of a database for susceptible difference-Mueller matrix elements. Additionally, the AMMS may further comprise a database of Mueller matrix elements to develop neural network models; and a backward-error propagation neural network algorithm module that provides pattern recognition of chemical-biological analytes built from the database of Mueller matrix elements. The AMMS may further comprise a self-organization map neural network algorithm module that provides type-classification of analyte species built from the database of Mueller matrix elements.

Another embodiment provides a method of performing data acquisition using an electronics AMMS that receives data from an infrared photopolarimetric-based DIAMMS chemical and biological remote sensor comprising a photoelastic-modulation engine and a computer, wherein the method comprises generating two primary and six overtone pure coherent sinusoidal frequencies to serve as reference waveforms; automatically maintaining a constant magnitude of optical backscattering intensity as the photoelastic-modulation engine permutes to one of a plurality of configurations; providing a plurality of Mueller (M) matrix elements as analog signals per fundamental/overtone frequency assignments in scattergram voltage waveforms detected by the remote sensor; digitizing the Mueller matrix analog signals; transmitting the digitized signals to the computer of the remote sensor; and using a GUI system to control the remote sensor. The plurality of configurations may comprise four configurations. Moreover, the plurality of Mueller (M) matrix elements may comprise eight Mueller (M) matrix elements. Additionally, an output of the plurality of Mueller (M) matrix elements is preferably proportional to a dot product between detected scattergram signals and each reference waveform.

Preferably, the GUI system comprises automatic control of (i) an optical system of the remote sensor, (ii) safety failsafe operations of the remote sensor, (iii) synchronized acquisition of Mueller matrix elements data, (iv) optimization of data measurements, and (v) preprocessing of acquired data and filtration of a database for susceptible difference-Mueller matrix elements. The method may further comprise developing neural network models using a database of Mueller matrix element; providing pattern recognition of chemical-biological analytes built from the database of Mueller matrix elements; and providing type-classification of analyte species built from the database of Mueller matrix elements.

Another embodiment provides an apparatus for performing data acquisition using an electronics AMMS that receives data from an infrared photopolarimetric-based DIAMMS chemical and biological remote sensor comprising a photoelastic-modulation engine and a computer, wherein the apparatus comprises means for generating two primary and six overtone pure coherent sinusoidal frequencies to serve as reference waveforms; means for automatically maintaining a constant magnitude of optical backscattering intensity as the photoelastic-modulation engine permutes to one of a plurality of configurations; means for providing a plurality of Mueller (M) matrix elements as analog signals per fundamental/overtone frequency assignments in scattergram voltage waveforms detected by the remote sensor; means for digitizing the Mueller matrix analog signals; means for transmitting the digitized signals to the computer of the remote sensor; and means for using a GUI system to control the remote sensor. The plurality of configurations may comprise four configurations. Furthermore, the plurality of Mueller (M) matrix elements may comprise eight Mueller (M) matrix elements. Preferably, an output of the plurality of Mueller (M) matrix elements is proportional to a dot product between detected scattergram signals and each reference waveform.

The GUI system preferably comprises automatic control of (i) an optical system of the remote sensor, (ii) safety failsafe operations of the remote sensor, (iii) synchronized acquisition of Mueller matrix elements data, (iv) optimization of data measurements, and (v) preprocessing of acquired data and filtration of a database for susceptible difference-Mueller matrix elements. Furthermore, the apparatus may comprise means for developing neural network models using a database of Mueller matrix element; means for providing pattern recognition of chemical-biological analytes built from the database of Mueller matrix elements; and means for providing type-classification of analyte species built from the database of Mueller matrix elements.

These and other aspects of the embodiments herein will be better appreciated and understood when considered in conjunction with the following description and the accompanying drawings. It should be understood, however, that the following descriptions, while indicating preferred embodiments and numerous specific details thereof, are given by way of illustration and not of limitation. Many changes and modifications may be made within the scope of the embodiments herein without departing from the spirit thereof, and the embodiments herein include all such modifications.

BRIEF DESCRIPTION OF THE DRAWINGS

The embodiments herein will be better understood from the following detailed description with reference to the drawings, in which:

FIG. 5A is a block diagram illustrating an AMMS according to an embodiment herein;

FIG. 5B is a block diagram illustrating a system used in accordance with the AMMS of FIG. 5A according to an embodiment herein;

DETAILED DESCRIPTION OF PREFERRED EMBODIMENTS

Figure 1:
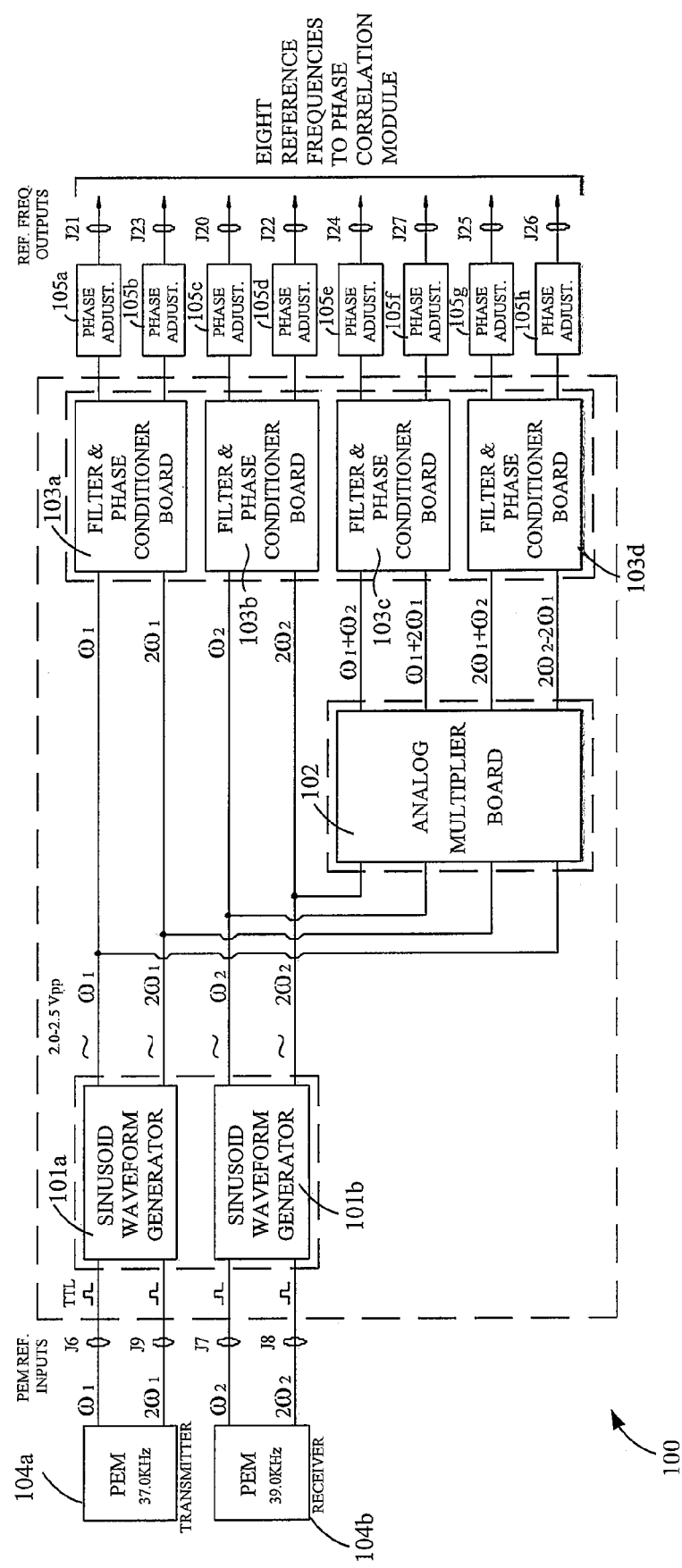
FIG. 1 is a block diagram illustrating a reference frequencies synthesizer module of an analog Mueller matrix system (AMMS) according to an embodiment herein.

The embodiments herein and the various features and advantageous details thereof are explained more fully with reference to the non-limiting embodiments that are illustrated in the accompanying drawings and detailed in the following description. Descriptions of well-known components and processing techniques are omitted so as to not unnecessarily obscure the embodiments herein. The examples used herein are intended merely to facilitate an understanding of ways in which the embodiments herein may be practiced and to further enable those of skill in the art to practice the embodiments herein. Accordingly, the examples should not be construed as limiting the scope of the embodiments herein.

The drawings and the descriptions herein refer to "J" type pins. This is for illustrative purposes to describe exemplary embodiments only. However, the embodiments herein are not restricted to any particular type of pin connection. Moreover, those skilled in the art would readily appreciate incorporating different type pin connectors, which may be used in accordance with the embodiments herein. Referring now to the drawings, and more particularly to FIGS. 1 through 7, where similar reference characters denote corresponding features consistently throughout the figures, there are shown preferred embodiments. The Mueller calculus derived by Hans Mueller is a matrix method for transforming a vertical array of four parameters called the Stokes vector which represent polarized, randomly-polarized, or partially-polarized electromagnetic fields in their magnitudes and relative phases. Transformation of the 1×4 Stokes vector defines the 4×4 Mueller matrix (M), the latter describing familiar phenomena such as reflection, refraction, absorption, and elastic scattering in toto. Accordingly, there are versatile applications for the precise measurement of this comprehensive 16-element metric for physical systems and biological structures. Of particular interest is the chemical-biological (CB) warfare agents standoff identification/detection problem, and resolving how information inherent in selective infrared energy-tuned M-elements vis-à-vis polarized elastic backscattering may be applicable toward a unique and viable solution. This subject addresses a U.S. Department of Defense standoff detection technologies initiative. In a previous experimental study/analysis, relevant to this issue, pure crystalline amino acids pressed into wafers—and other surfaces—were characterized by a technique called differential-absorption Mueller matrix spectroscopy (DIAMMS) as fully set forth in the above-referenced patents as well as in U.S. Pat. Nos. 5,659,391; 6,060,710; and 6,389,408, the complete disclosures of which, in their entireties, are herein incorporated by reference, and which generally teach photopolarimetric lidar dual-beam switching devices and Mueller matrix standoff detection systems and methods. Current interest extends this same technology/methodology toward detecting Biological Safety Level-1 aerosols including γ-irradiated *Bacillus Subtilis* (a nonviable bacterium and useful model simulant for the biological warfare agents) and chicken egg Albumin (water soluble protein and secondary biological agent simulant), in situ, in an ambient environment. Accordingly, experiments were designed requiring an upgrade of the original infrared dual polarization-modulation based DIAMMS photopolarimetric sensor hardware, integrating it to an aerosol chamber, and re-establishing certain DIAMMS measurement protocols with modified/additional software for this aerosol standoff identification/detection feasibility study.

The basic DIAMMS method is as follows. Sequential laser band-tuning/detuning in the alternate beam square-waveform [... L1:L2 ...], on the peak/tail of molecular absorption band of subject aerosol target, prompts a sub-field of susceptible differential-backscattering elements $\{\Delta M'\} = \{M^a_{ij}/M^a_{11} - M^r_{ij}/M^r_{11}\}$ unique to the analyte (analyte is the aerosol targeted for identification) that are cued; where superscripts a and r signify absorption and reference, respectively, and subscripts i,j ∈ 1, 2, 3, 4≠1,1; viz, the grouped non-[1,1] Mueller elements. Mathematical rules which dictate the subclass of Mueller elements that are members of a specific analyte's susceptance class comprising $\{\Delta M'\}$ are given in Carrieri, A. et al., "Photopolarimetric lidar duel-beam switching device and Mueller matrix standoff detection method," J. Appl. Remote Sens., Vol. 1, 013502, pp. 1-23, Jan. 19, 2007, the complete disclosure of which, in its entirety, in herein incorporated by reference. Subsequent to the empirical measurement of this data set, $\{\Delta M'\}$, a domain with dimension between 1 and 15 modulo the 2-laser beam probing wavelengths L1 and L2 are constructed. The dimension of domain is also the cardinal number of a susceptance class that associates a specific analytic aerosol species A, B, C, ... etc. Each analyte occupies a unique domain in Mueller space—its fingerprint identification feature. In the DIAMMS standoff detection scheme, moreover, identification/detection events are positive whenever a one-to-one mapping is established between (preprocessed) data output by the photopolarimetric sensor and the Mueller domain of subject backscatterer A, B, C, ... etc. The latter mapping action can be performed, for instance, by a properly trained and validated neural network.

The embodiments herein provide an electronic analog Mueller matrix system (AMMS) required for operation of a photopolarimetric sensor, Mueller matrix database production, and neural network modeling. The AMMS electronics hardware and software embodiments are components of the photopolarimeter sensor, which are necessary for fully evaluating DIAMMS methodology and feasibility of infrared polarized scattering technology for CB defense.

The dual photoelastic-modulation (PEM) engine of a DIAMMS sensor, driven by the AMMS, delivers a complex temporal voltage waveform signal output called a scattergram, i(t), which is a manifestation stress-induced birefringence in its two ZnSe crystals compressed-then-relaxed at their natural mechanical resonance at high frequencies via bonded opposing transducer elements. The Fourier transform of i(t) takes on a general functional form expressed as:

$$I = I_{dc} + I_{ac}(n\nu_1, k\nu_2, n\nu_1 \pm k\nu_2, \Sigma(\nu_1,\nu_2)) \quad (1)$$

where $I_{dc}$ is the phase-insensitive (scalar) term of scattergram tracking element [1,1] of Mueller matrix M, $I_{ac}$ its phase-sensitive (altering vector) term that tags all other 15 M-elements one-to-one, and PEM transmitter and receiver driver frequencies are $\nu_1$=37 KHz and $\nu_2$=39 KHz; respectively—a 2 KHz offset is important regarding displacement of overtones in I and their electronic accessibility.

The exact mathematical expansion of $I_{ac}$ is a convergent infinite series in terms of powers of the PEM transducer frequencies. The higher-order overtones $\Sigma(\nu_1,\nu_2)$ are naturally attenuated by Bessel coefficients of increasing power and, furthermore, harmonics greater than 100 KHz are suppressed by electronic filtration in the AMMS. Accordingly, the dominant first three terms in Equation 1 comprising of primary components $\nu_1$, $\nu_2$, and the first-order overtones n, k=integers 1 and 2, are most relevant. They comprise the scattergram primaries and harmonics in circular frequency terms of $\omega_1$, $\omega_2$, $2\omega_1$, $2\omega_2$, $\omega_1 \pm \omega_2$, $\omega_1 \pm 2\omega_2$, $2\omega_1 \pm \omega_2$, $2\omega_1 \pm 2\omega_2$; each of which tag a distinct individual non-[1, 1] M-element. Meanwhile, the phase insensitive term of scattergram, $I_{dc}$, corresponds precisely to the [1, 1] element of M and vice versa. Determination of the 15 non-[1, 1] M-elements is equivalent to a sensing phase from first-order overtones in $I_{ac}$ via standard lock-in detection methods. Moreover, an additional $I_{dc}$ lock-in amplification measurement for element [1, 1] is preformed separately yet concurrent to the phase-sensitive M-elements detection measurement.

The AMMS facilitates these Mueller data acquisitions, directly from the photopolarimeter's scattergram signal i(t), through integrated electronic circuits and their supporting software performing these ordered operations: (1) frequency synthesis for providing reference inputs to 8 phase-sensitive-detectors; (2) automated feedback for regulation of scattergram intensity; (3) phase correlation for convolution of M-elements; and (4) data digitization and computer communication protocols for acquisition, preprocessing, and management of incoming sensor data streams. A brief description of each of these operations and the integrated electronics modules that perform these operations is provided below.

Figure 2:
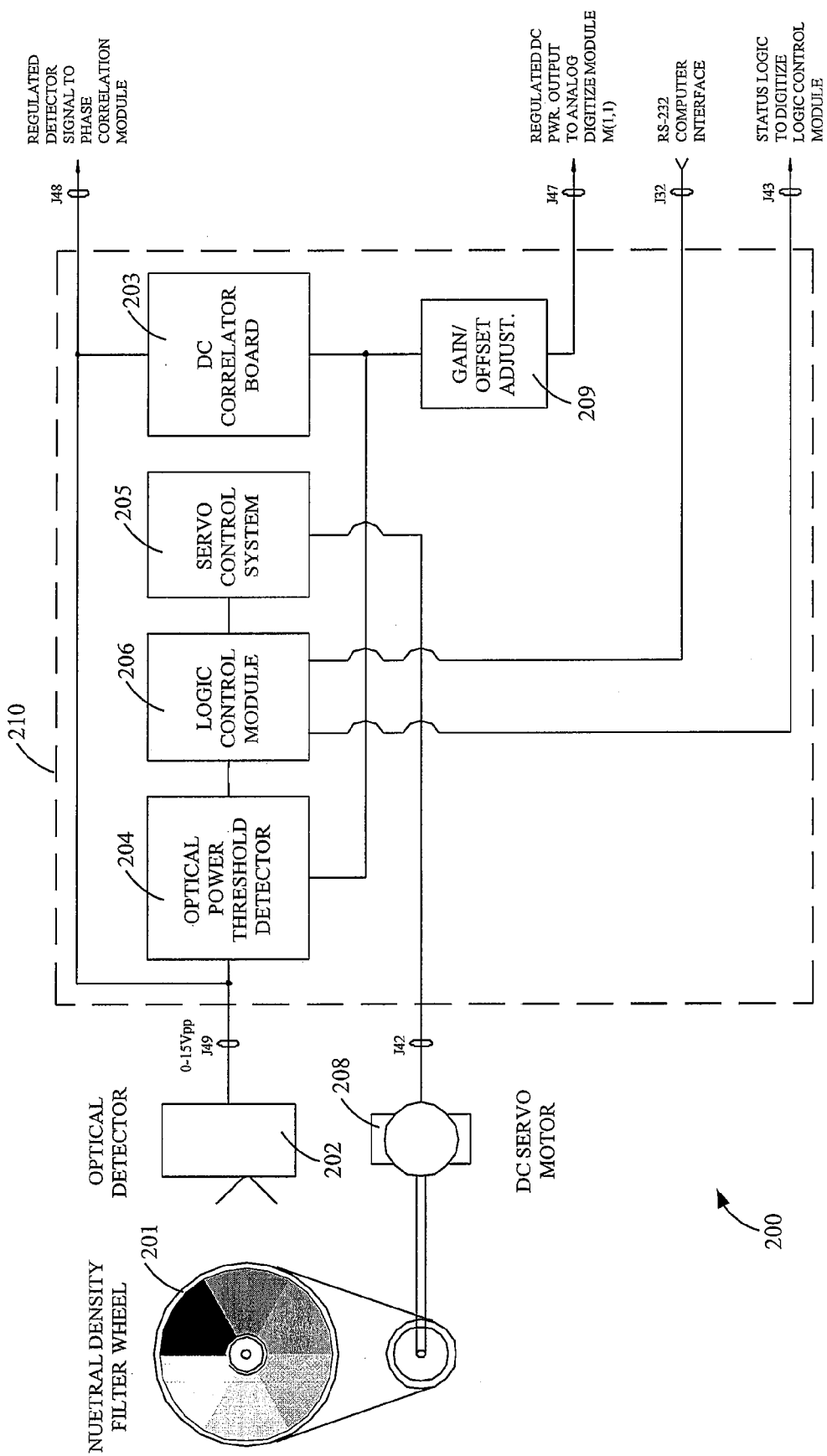
FIG. 2 is a block diagram illustrating the scattergram intensity regulation and control module of an AMMS according to an embodiment herein.
Figure 3:
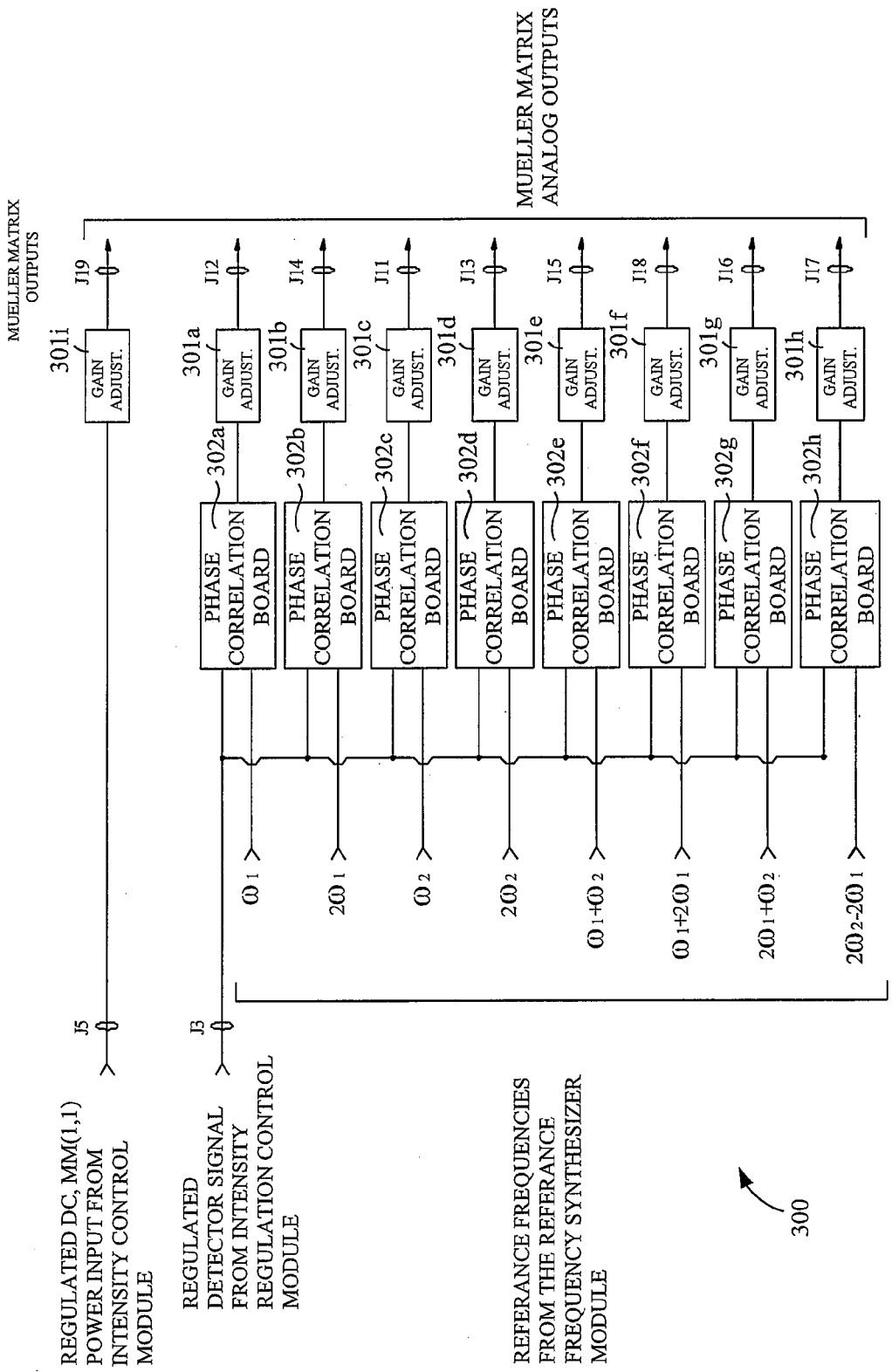
FIG. 3 is a block diagram illustrating the phase correlation module of an AMMS according to an embodiment herein.

A reference frequency synthesizer circuit module 100 is illustrated in FIG. 1, and is the front-end of the AMMS 500 (of FIG. 5A) providing precision reference-frequency inputs that are required for phase-lock detection of the M-elements via the phase correlation module 300 (of FIG. 3). Module 100 comprises sinusoid waveform generator 101a, 101b, analog multiplier 102, and filter-phase conditioner 103a-103d. The sinusoid waveform generator 101a, 101b receives four sets of reference pulses in square-wave form from two PEM controller units 104a, 104b of a photopolarimetric sensor 210 (of FIGS. 2 and 5A)—primary driving frequencies: $\upsilon_1=37$ Khz and $\upsilon_2=39$ Khz; and their doubled frequencies: $2\upsilon_1$ (74.0 Khz) and $2\upsilon_2$ (78.0 Khz)—then shapes and smoothes them into precise sinusoids $\omega_1$, $\omega_2$, $2\omega_1$ and $2\omega_2$ via waveform generators 101a, 101b. The analog multiplier circuit 102, on receiving $\omega_1$, $\omega_2$, $2\omega_1$ and $2\omega_2$ from generators 101a, 101b, outputs the overtones $\omega_1\pm\omega_2$, $\omega_1\pm2\omega_2$, $2\omega_1\pm\omega_2$, and $2\omega_1\pm2\omega_2$ (± signifies each overtone exhibit bands 180 degrees out of phase from the other). These overtone bi-products are then passed through a band-pass filter 103a-103d that eliminate side bands, extract, and pass the pure components $\omega_1+\omega_2$ (76.0 Khz), $\omega_1+2\omega_2$ (115.0 Khz), $2\omega_1+\omega_2$ (113.0 Khz), and $2\omega_1-2\omega_2$ (4.0 Khz) that accommodate the phase correlation boards 302a-302h of module 300 (of FIG. 3) specifically tuned to these frequencies. Finally, all eight reference frequencies $\omega_1$, $\omega_2$, $2\omega_1$, $2\omega_2$, $\omega_1+\omega_2$, $\omega_1+2\omega_2$, $2\omega_1+\omega_2$, and $2\omega_1-2\omega_2$ are adjusted in precise relative amplitude (2.0-2.5 Vp-p) and phase (0 to 180 degrees) via a plurality of potentiometers 105a-105h (for example, eight potentiometers 105a-105h shown in FIG. 1), as the waveforms are displayed on the screen of an oscilloscope 501 (of FIG. 5A) during calibration of the AMMS 500 (of FIG. 5A) through 50 ohm BNC style connectors (not shown) through pins J20-J27 (of FIG. 1).

FIG. 2 illustrates a scattergram intensity regulation and control module 200. In order to produce a full field of 16 M-elements from a photopolarimeter, a series of four distinct optical permutations in its (POL-PEM)$_t$:(PEM-POL)$_r$ Mueller matrix engine is utilized; where the colon is a reference junction of these permutations through which a sequence of four distinct 45-degree rotations is enacted by the AMMS 500 (of FIG. 5A). A fixed optical intensity in the phase-insensitive [1, 1] Matrix element scalar signal ($I_{dc}$, Equation 1) of scattergrams is preferably maintained between permutation sequencing, and just before initiating digitization of the first batch of nine M-elements via phase correlation module 300 (of FIG. 3) of the AMMS 500 (of FIG. 5A). Regulation proceeds directly on the scattergram intensity, $<|i(t)|>$, as that backscattering radiance is received from the HgCdTe photoconductive detector 202 of a DIAMMS sensor 210.

In module 200, the rotating ZnSe variable neutral density filter wheel 201 is shown to display 90 degrees out of its plane, and is positioned directly before the sensor's parabolic focusing optic 202. This optic 202 evenly and linearly regulates 9-12 μm infrared throughput radiance as received from switched incident laser beams . . . L1:L2 . . . backscattered from subject material (aerosol plume). Regulation attains-then-maintains constant voltage amplitude in the scattergram $I_{dc}$ signal intensity, within the dynamic range (2.0 to 3.0 $V_{dc}$) of a current-biased preamplifier product connected to HgCdTe detector chip (sensor's photoreceptor) during (POL-PEM)$_t$:(PEM-POL)$_r$ permutation actions of a photopolarimeter. A feedback loop, moreover, prevents i(t) output from drifting below (under-attenuation) and above (saturation) a specified $V_{dc}$ setting, usually the midpoint of dynamic range in the HgCdTe preamplifier.

The automated optical power regulator control system 200 of FIG. 2 comprises optical detector 202 (HgCdTe/amplifier); electronic DC ($I_{dc}$) correlate board 203; optical power threshold detector circuit 204; electromechanical servo-control system 205; electronic logic control circuit 206; a gain/offset adjustment circuit 209; and servo-driven circular ZnSe variable neutral density attenuator optic (wheel) 201. Input to the DC correlate board 203 is i(t) from the optical detector 202 through J49, 2 50-ohm BNC connector. This is the scattergram voltage waveform transmitted to a biased impedance-matched preamplifier vis-à-vis the sensor's HgCdTe photoconductive chip (not shown) located on focus of the sensor's telescopic Cassegrain receiver (not shown). The DC correlate circuit 203 convolutes the output of preamplifier (Equation 1) onto itself, producing a DC output proportional to the sum of the absolute value of the total power associating each positive and negative lobe of i(t) controlled by the module 200 of the AMMS 500 (of FIG. 5A). This is an unconventional utilization of an existing phase-sensitive electronic for generating average optical power density. The utilization of a phase correlator board 203 to generate an average optical power value is unique for this process. This method is chosen over more traditional averaging methods in an effort to determine the average optical power of the AC components of the scattergram waveform only, as they are produced by the detector 202, thereby rejecting its DC components. The AC components contain the energy of the modulated waveforms of interest, whereas the DC component contains non-modulated energy such as unwanted background optical energy and biasing voltages.

The average optical power signal, or DC element, produced by the DC correlator 203, is accessible through, J47, which is located on the rear panel 514 (of FIG. 5E) of the automated optical power regulator control system 200 (of FIG. 2), as well as through, J19 which is located on the front panel 511 (of FIG. 5D) of the AMMS 500 (of FIG. 5A). Both electrical interfaces may utilize a 50 ohm BNC style connector. The gain/offset adjustment module 209 (of FIG. 2) is utilized to condition the correlator board's DC output with a gain and offset capability. The amplitude and offset of the DC value is adjustable through two potentiometers 512, 513 located on the front panel 511 of the AMMS 500. Amplitude and offset adjustments of the DC element is utilized during the AMMS calibration procedure.

Again with reference to FIG. 2, through action by the optical power threshold detector 204, the regulation function of module 200 can accommodate relatively mild variance in i(t) (e.g., due to turbulence in the aerosol plume and Brownian motion of particles within the solid angle of irradiating beam), as well as more abrupt swings in i(t) (e.g., when the DIAMMS sensor 210 is suddenly aimed at high-reflectance surfaces such as terrain and synthetic surfaces like asphalt, concrete, . . . etc). To accomplish this, the threshold detector 204 continually monitors average signal output by the DC correlate circuit 203, and notifies logic control circuit 206 should intensity of the scattergram stray significantly from the allowed dynamic range of the preamplifier. Should that range be reached and exceeded, the logic control circuit 206 activates the servo control system 205 so as to bring backscattering intensity in the $I_{dc}$ voltage signal back to the optimum level for M-elements measurement (ibid, mid-point of HgCdTe preamplifier's dynamic range) and maintain that level (voltage), when enabled, via communications through J32 (pin 4), RTS line J32 (pin 1).

The following series of actions are then preformed, as they are linked between the threshold detector 204 output and the electromechanical-controlled variable neutral density filter wheel 201: (1) neutral density filter optic 201 is driven in clockwise or counterclockwise directions vis-à-vis the servomotor 208 and control system 205; (2) control system 205 continually drives servomotor 208 until power measured by the DC correlate circuit 203 (vis-à-vis the DIAMMS optical HgCdTe detector 202) and preset $I_{dc}$ power setting (vis-à-vis the threshold detector 204) equate; (3) when equal, a brake-rotation action is executed thus stopping the variable neutral-density optic 201 via the logic control circuit 206 signaling the servo-controller 205 to halt. At this time, i(t) is fixed in backscattering intensity, the threshold detector 204 is disabled via the logic control circuit 206, and the backscattering radiant intensity is established at optimum throughput.

Consequently, the AMMS 500 (of FIG. 5A) opens its analog-to-digital converter channels and enables a 6.0 Hz pulse train for commencing measurement of a set of 9 M-elements (all channels digitized simultaneously). These M-element data records are fed through serial interface port J32 (pin 3 of FIG. 2), whereby transmission-recording of M-elements commence, as long as the 'High' state exists, in the RTS control line between control computer 502 (of FIG. 5A) of the photopolarimetric sensor 210 and module 200. A 'Low' logic level on this RTS line signals sufficient M-elements were acquired, by the CPU 502 (of FIG. 5A), through port J32 (pin 3) and recorded, thereby disabling the 6.0 Hz digitizer strobe pulse train. At this time the first group of M-elements are recorded on disk and all logic paths between sensor 210, its central control computer 502 (of FIG. 5A), and module 200 are subsequently reinitialized so as to repeat the entire M-elements acquisition sequence at a succeeding (POL-PEM)$_t$: (PEM-POL)$_r$ permutation of the DIAMMS sensor's photopolarimeter engine (not shown). All of these regulation control functions discussed occurring via module 200 are monitored externally and accessible on the front and rear-panels 511 (FIG. 5D), 510 (FIG. 5C), respectively, of the AMMS 500 (of FIG. 5A) through 50 ohm BNC connectors. In FIG. 2, J48 is an output comprising the optical detector complex signal waveform which is utilized as a signal source for the phase correlator detection module 300 (of FIG. 3). The output, J48, is an electrical duplicate of the detector input signal present at J49 (of FIG. 2). The two electrical connectors are connected in parallel as to produce a loop-through function. J47 is an output comprising of the average optical power signal, or DC Mueller Matrix element M(1,1), and is produced by the DC correlator board 203. The output is accessible on the front panel 511 (of FIG. 5D) of the AMMS 500 (of FIG. 5A) through a 50 ohm BNC connector. The fain/offset adjustment block 209 (of FIG. 2) resident to the DC power regulator optical control system (module 200) is utilized to condition the correlator board's DC output with a gain and offset capability. The amplitude and offset of the DC value, (Mueller Matrix element M(1,1), is adjustable through the two potentiometers 512, 513 located on the front panel 511 of the AMMS 500. Amplitude and offset adjustments of the DC element is utilized during the AMMS calibration procedure.

The phase correlate (Mueller matrix detection) module 300 of the AMMS 500 (of FIG. 5A) is illustrated in FIG. 3. Module 300 produces M-elements through a suite of a plurality of phase-sensitive detection boards (PSDBs) 301a-301h (for example, eight PSDBs 301a-301h) as shown in FIG. 3. The input to each PSDB 301a-301h is one of eight reference frequencies from the reference frequency synthesizer module 100 (of FIG. 1), and the real-time scattergram voltage output from the HgCdTe detector/preamplifier of photopolarimeter delivering the real-time scattergram signal i(t) of photopolarimetric sensor 210 (of FIG. 2). Output by the PSDB 301a-301h is the actual analog Mueller matrix signal assigned to it given by:

$$M_{ij}^{out} = \frac{1}{\tau}\int_{t-\tau}^{t}[\sin\omega_{ref(ij)}\cdot\xi + \varphi]i(\xi)d\xi \qquad (2)$$

where the phase term φ is adjusted during sensor calibration procedure via potentiometers (not shown) located on the front panel 511 of the AMMS 500, and τ (approximately 0.16 s) is the period of integration over which simultaneous Mueller elements $M_{ij}$ measurements are made at their associative lock-in frequencies $\omega_{ref(ij)}$. The PSDB 301a-301i is embodied as a signal convolver or dot product computer which produces an analog output (Mij out) equivalent to the product of the amplitude of the scattergram waveform signal i(t), the input reference frequency w$_{ref}$(ij), and the cosine of the phase angle difference between those two signals. It is also a very narrow, high gain, band pass filter that extracts generally weak M-elements signal at reference (carrier) frequency $\omega_{ref(ij)}$ from a generally noisy scattergram voltage waveform i(t). The analog outputs $M_{ij}$out generated by the suite of eight phase PSDBs 301a-301h, module 300, is accessible on the AMMS front panel chassis (not shown) through eight 50 ohm BNC connectors (not shown) through pins J11-J18. The gain adjustment blocks 302a-302h is utilized to condition the output of each phase sensitive detection board resident to the phase correlator module 300 (of FIG. 3), thereby providing a variable gain (amplitude) capability to the Mueller Matrix outputs. The amplitude of each of the analog Mueller Matrix outputs is adjustable through a potentiometer 512, 513 located on the front panel 511 of the AMMS 500. Amplitude adjustment of the Mueller Matrix elements is utilized during the AMMS calibration procedure.

Figure 4:
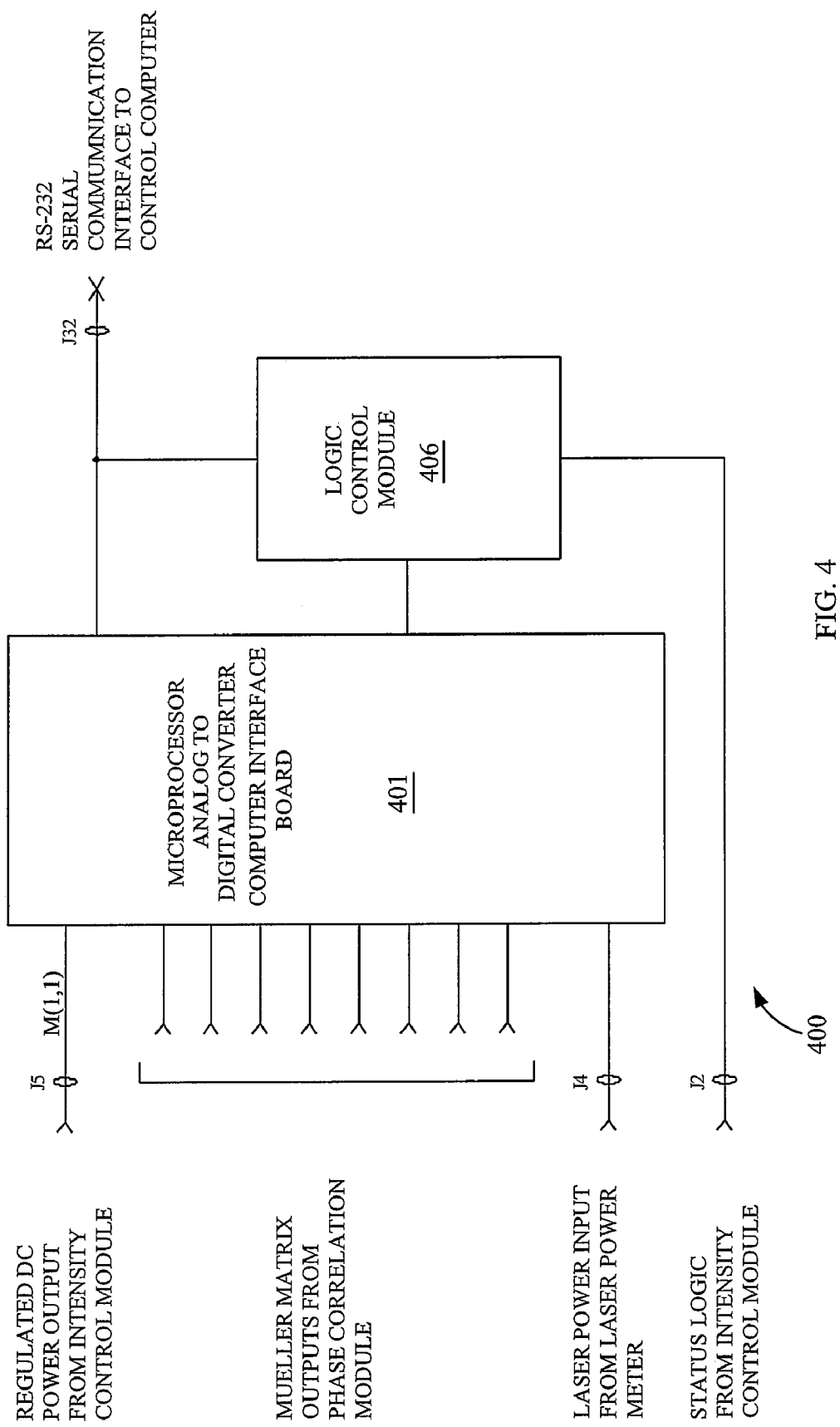
FIG. 4 is a block diagram illustrating the data digitization and computer interface module of an AMMS according to an embodiment herein.
Figure 5C:
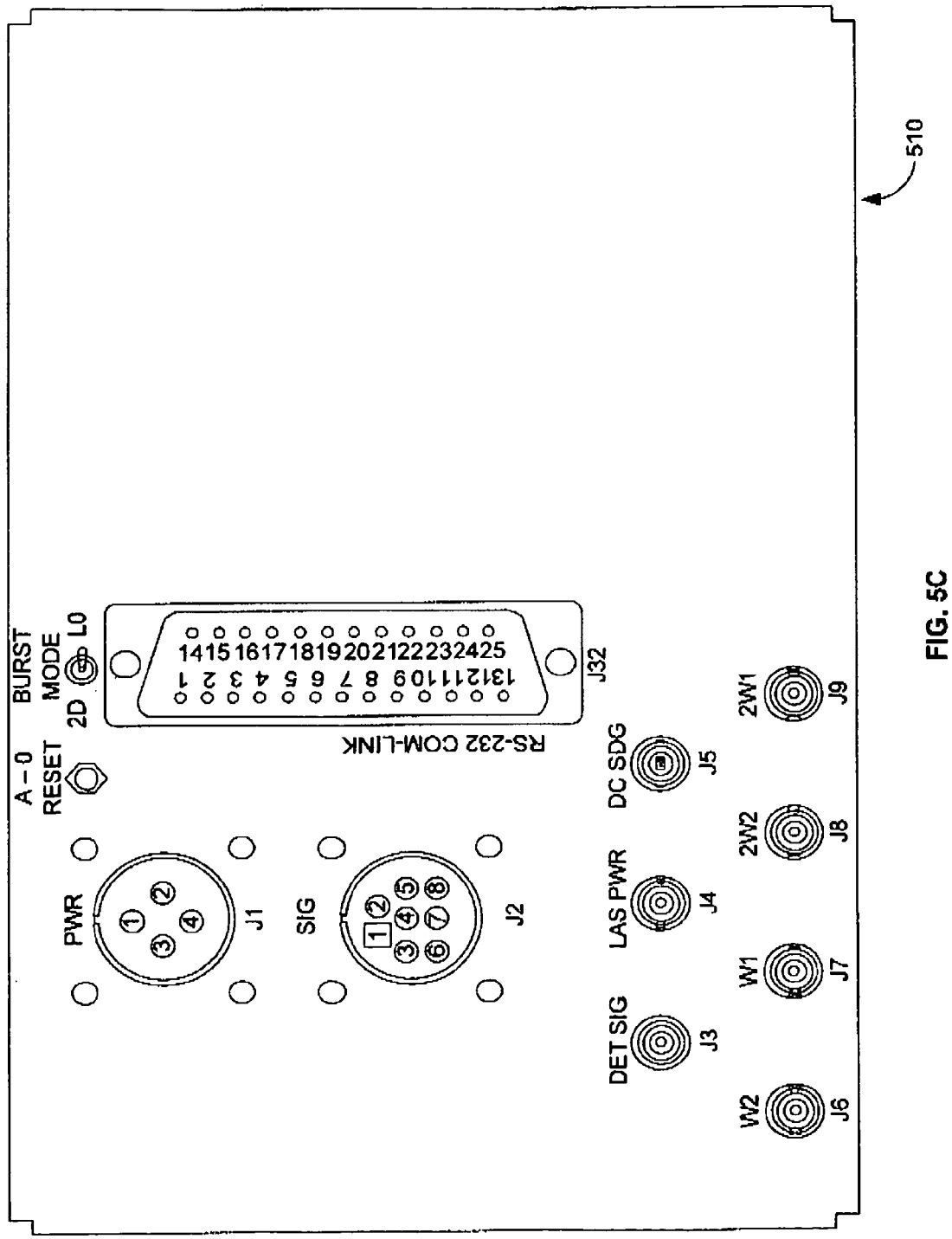
FIG. 5C is a schematic diagram illustrating a rear panel of the AMMS of FIG. 5A according to an embodiment herein.
Figure 5D:
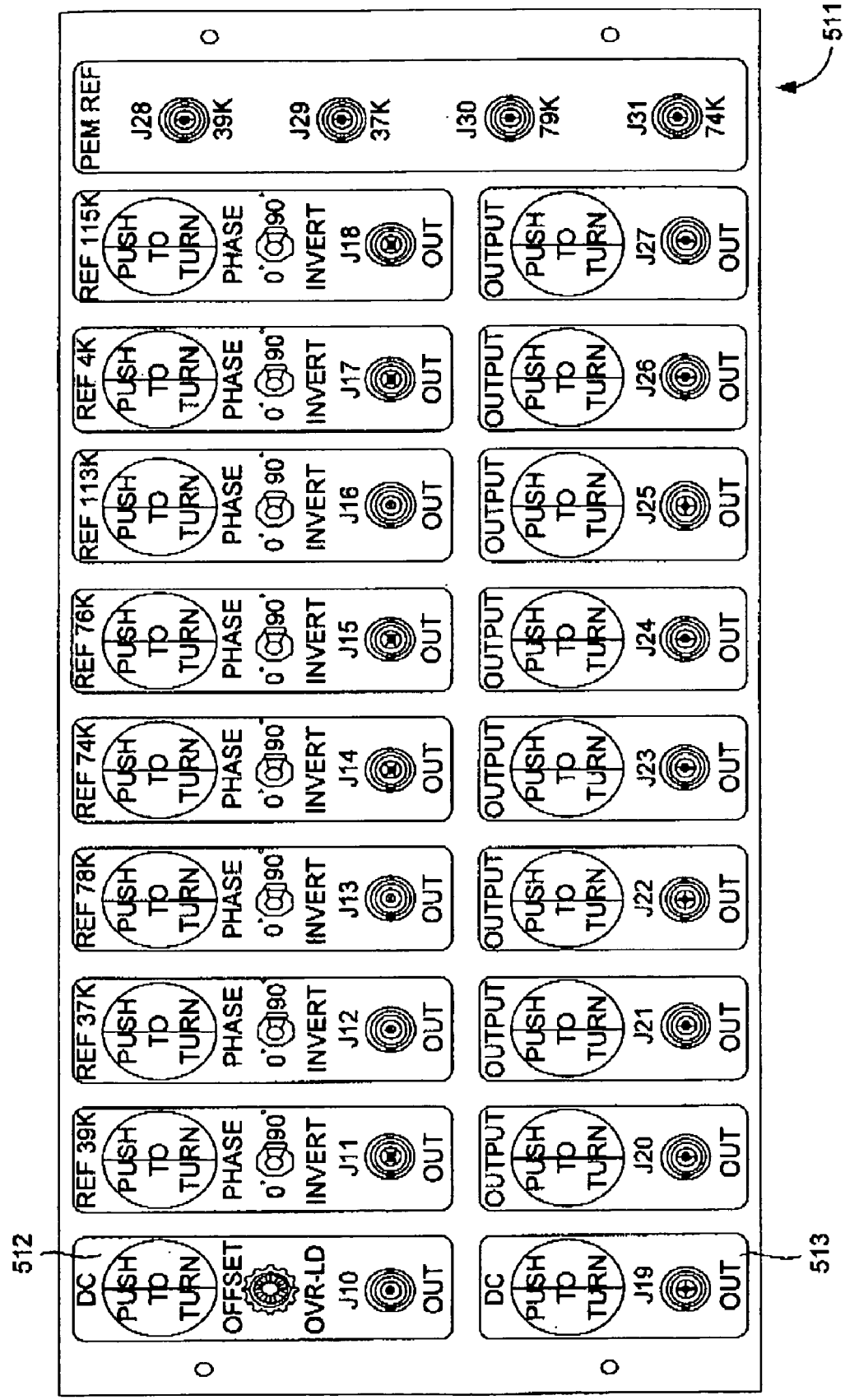
FIG. 5D is a schematic diagram illustrating a front panel of the AMMS of FIG. 5A according to an embodiment herein.
Figure 5E:
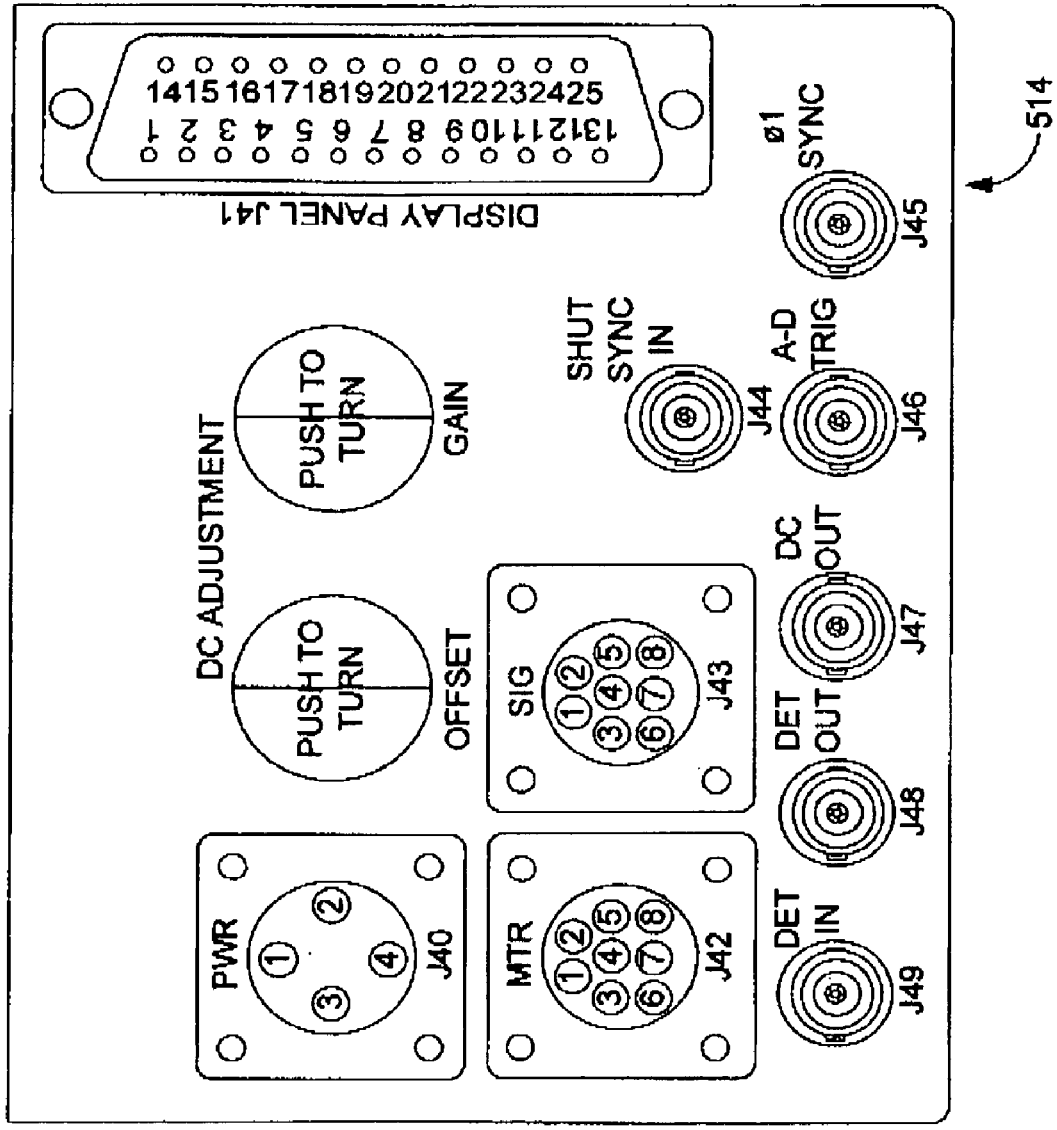
FIG. 5E is a schematic diagram illustrating a rear panel of the automated optical power regulator control system of FIG. 2 according to an embodiment herein.

The data digitizer and computer interface module 400 of AMMS 500 (of FIG. 5A) comprises of a stand-alone microprocessor, analog-to-digital converter, and computer interface board 401, as shown in FIG. 4. This circuit 400 is configured to digitize ten individual analog signals: the received backscatter optical power $I_{dc}$ (i.e., Mueller element [1,1]); eight phase-sensitive M-elements data channeled via module 300 (of FIG. 3); and optical power of a laser beam from the incident train [ . . . L1:L2 . . . ].

Digitization is initiated by receipt of the 6.0 Hz strobe pulse train enacted via the logic control circuit 406 (i.e., when optimum gain of i(t) is established via the intensity and regulation control circuit 200 (of FIG. 2). These data are structured into strings of two's complement hexadecimal format and then serially transmitted to the DIAMMS central control computer 502 (of FIG. 5A) at a fixed rate of six strings per second. After the central computer 502 receives sufficient quantity of these 6 Hz data strings—this logic is actually dictated by operator input via a graphical user interface (GUI) command used when initializing a particular sensor measurement trial—the 'cease digitization' command, also sent by the logic control circuit 206 (of FIG. 2), disables the strobe 6 Hz data stream. The DIAMMS central control computer 502 enables/disables data acquisition actions accordingly, in the precise manner described above, via serial port J32 utilizing pins P-2 (transmit), P-3 (receive), P-7 (ground), and P-4 (RTS)—all traffic in these pins can be accessed and monitored from a connector (not shown) located on the rear panel 510 of the AMMS 500.

FIGS. 5A and 5B are block diagrams of the AMMS integration and operation DIAMMS sensor system 500. The AMMS mainframe 505 of FIG. 5A comprises modules 100-400 (of FIGS. 1 through 4). Primary and doubled frequencies $\omega_1$, $\omega_2$, $2\omega_1$, and $2\omega_2$ output by the reference frequency synthesizer circuit (embedded in the mainframe 505) are externally accessible from four BNC connectors (not shown) located at the far right side of the faceplate of the mainframe 505. The eight channels of disparate M-elements measurements ($M_{ij}^{out}$) via PSDBs 301a-301i (of FIG. 3) are also externally accessible via BNC connectors, also provided on the faceplate of the mainframe 505. Moreover, individual adjustments of PSDB signal phase and amplitude, per M-element channel output, are made through another set of potentiometer pots (not shown) located just above the BNC connectors (not shown). Adjustments are performed via an elaborate calibration procedure of the photopolarimeter (not shown), where the M-elements of known rotating optics are matched to AMMS outputs; e.g., the waveforms of elements representing rotating infrared linear polarizer and/or quarter-wave plate, inserted into the optical path of sensor, are precisely matched one-to-one onto their known M-elements directly from outputs of the phase correlation module 300.

The Mueller element [1, 1] is measured directly from a separate lock-in detection board 504 embedded inside the AMMS mainframe 505. This direct readout of $I_{dc}$ is delivered via the scattergram intensity regulation and control circuits of module 200—adjacent to the oscilloscope 501 and the rack-mounted electronics console 506 (of FIG. 5B) adjacent to a computer screen 507 (of FIG. 5B). A reading of $I_{dc}$=2.146 V, which may be displayed on the voltmeter 503 adjacent to the AMMS mainframe 505, is a result of module 200 (of FIG. 2) optimizing and stabilizing scattergram signal i(t). This regulation action is monitored in real-time on the console 506 (of FIG. 5B). Data acquisition commences when this level $I_{dc}$=2.146V is attained (optimized intensity in i(t)) terminated through via the logic control circuit 206 (of FIG. 2) . . . ad fin . . . until all desired M-elements of experiment are in storage (e.g., on computer disk).

The oscilloscope 501 in FIG. 5A portrays: (bottom trace 508) backscattering scattergram signal i(t) conducted from the photopolarimeter's AC-coupled preamplifier; and (top trace 509) its Fourier transformation (Equation 1). In the Fourier transform there are three dominant overtones which associate M-elements [1,2], [2,2], and [1,4] of aerosol backscatterer, respectively.

A computer command and control ($C^3$) system executing a main GUI on computer screen 507 (of FIG. 5B) meets the needs of managing operations of the AMMS modules 100-400 as they are linked to DIAMMS sensor optical embodiments. When the GUI is executed, icons and widgets representing main optical and electronic components of the DIAMMS photopolarimetric detection system (sensor 210) (of FIG. 5A) are presented on computer screen 507, as well as run-time and status informational content during the actual run of an experiment. The hardware components of the sensor 210 (of FIGS. 2 and 5A) graphically represented include: its optomechanical switch (OMS); lasers L1 and L2 positioned to sides of the OMS, two optical spectrum analyzers (OSAs) used for tuning beams L1 and L2, and optical orientation of photopolarimeter engine (POL-PEM)$_l$:(PEM-POL)$_r$.

The $C^3$ system choreographs all sensor protocols through the GUI via widgets and radio buttons. Accordingly, all pertinent information of sensor operations and data acquisition sequences are displays on the computer screen 507 including: current status of OSD output, photopolarimeter and waiting time per change of its optical orientation; number of groups of M-elements measured and options for measurement (all 16 M-elements or a subfield of elements); interactive numerical data display of M-elements at analytic (L1) and reference (L2) beams wavelengths with time-stamps; calibration status (e.g., the tuning beams L1 and L2 to their proper resonance-reference wavelengths and other sensor initialization tasks); start of a M-elements measurement sequence; and termination of experiment. The GUI can be operated inactively, in progress of an experimental run, and comprises various safety and failsafe mechanisms. The GUI is comprised of software modules executed through dialog scripts as code objects.

The techniques provided by the embodiments herein may be implemented on an integrated circuit chip (not shown). The chip design is created in a graphical computer programming language, and stored in a computer storage medium (such as a disk, tape, physical hard drive, or virtual hard drive such as in a storage access network). If the designer does not fabricate chips or the photolithographic masks used to fabricate chips, the designer transmits the resulting design by physical means (e.g., by providing a copy of the storage medium storing the design) or electronically (e.g., through the Internet) to such entities, directly or indirectly. The stored design is then converted into the appropriate format (e.g., GDSII) for the fabrication of photolithographic masks, which typically include multiple copies of the chip design in question that are to be formed on a wafer. The photolithographic masks are utilized to define areas of the wafer (and/or the layers thereon) to be etched or otherwise processed.

The resulting integrated circuit chips can be distributed by the fabricator in raw wafer form (that is, as a single wafer that has multiple unpackaged chips), as a bare die, or in a packaged form. In the latter case the chip is mounted in a single chip package (such as a plastic carrier, with leads that are affixed to a motherboard or other higher level carrier) or in a multichip package (such as a ceramic carrier that has either or both surface interconnections or buried interconnections). In any case the chip is then integrated with other chips, discrete circuit elements, and/or other signal processing devices as part of either (a) an intermediate product, such as a motherboard, or (b) an end product. The end product can be any product that includes integrated circuit chips, ranging from toys and other low-end applications to advanced computer products having a display, a keyboard or other input device, and a central processor.

The embodiments herein can take the form of an entirely hardware embodiment, an entirely software embodiment or an embodiment including both hardware and software elements. The embodiments that are implemented in software include but are not limited to, firmware, resident software, microcode, etc.

Furthermore, the embodiments herein can take the form of a computer program product accessible from a computer-usable or computer-readable medium providing program code for use by or in connection with a computer or any instruction execution system. For the purposes of this description, a computer-usable or computer readable medium can be any apparatus that can comprise, store, communicate, propagate, or transport the program for use by or in connection with the instruction execution system, apparatus, or device.

The medium can be an electronic, magnetic, optical, electromagnetic, infrared, or semiconductor system (or apparatus or device) or a propagation medium. Examples of a computer-readable medium include a semiconductor or solid state memory, magnetic tape, a removable computer diskette, a random access memory (RAM), a read-only memory (ROM), a rigid magnetic disk and an optical disk. Current examples of optical disks include compact disk—read only memory (CD-ROM), compact disk—read/write (CD-R/W) and DVD.

A data processing system suitable for storing and/or executing program code will include at least one processor coupled directly or indirectly to memory elements through a system bus. The memory elements can include local memory employed during actual execution of the program code, bulk storage, and cache memories which provide temporary storage of at least some program code in order to reduce the number of times code must be retrieved from bulk storage during execution.

Input/output (I/O) devices (including but not limited to keyboards, displays, pointing devices, etc.) can be coupled to the system either directly or through intervening I/O controllers. Network adapters may also be coupled to the system to enable the data processing system to become coupled to other data processing systems or remote printers or storage devices through intervening private or public networks. Modems, cable modem and Ethernet cards are just a few of the currently available types of network adapters.

Figure 6:
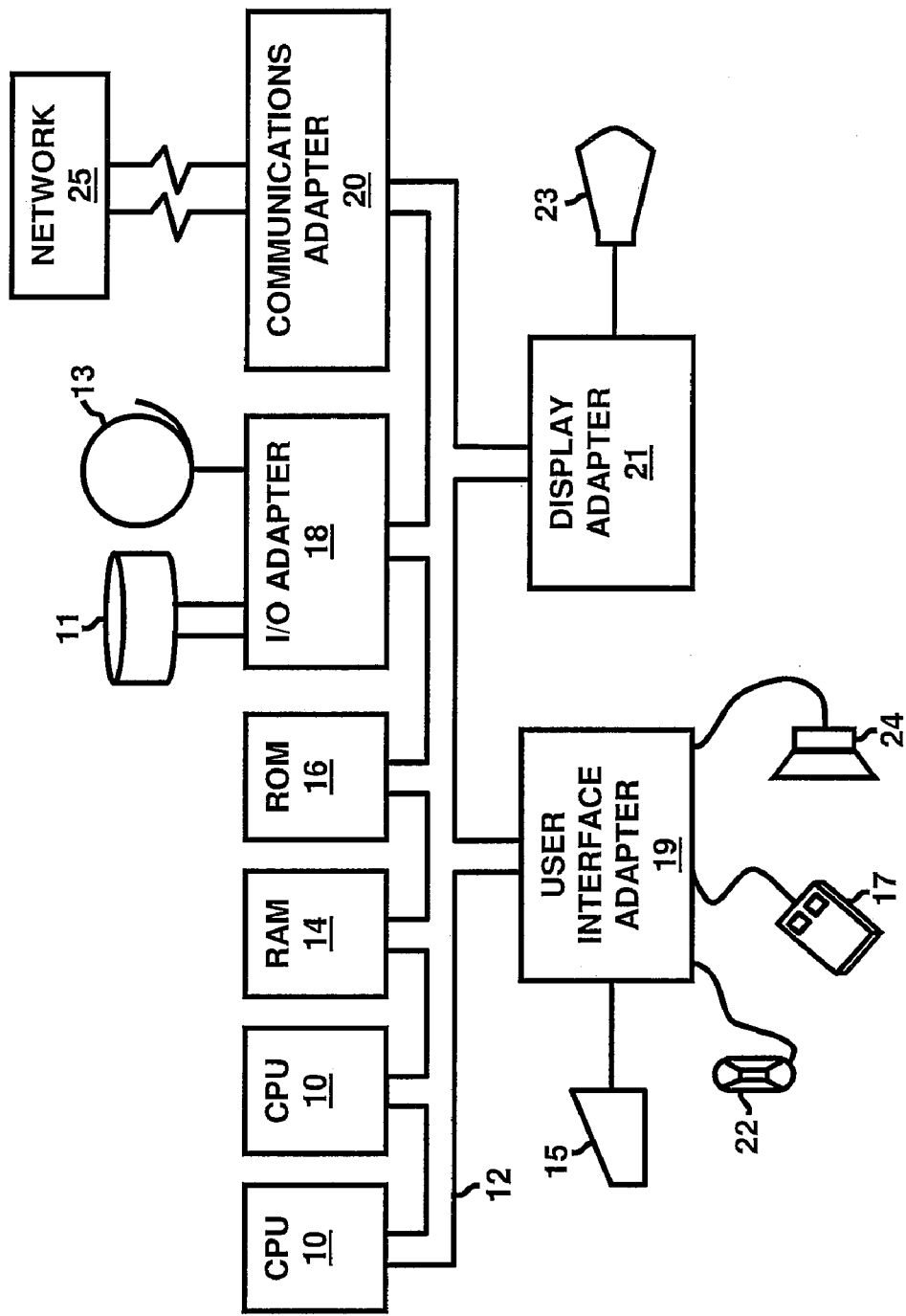
FIG. 6 is a block diagram of a computer system used in accordance with the embodiments herein.

A representative hardware environment for practicing the embodiments herein is depicted in FIG. 6. This schematic drawing illustrates a hardware configuration of an information handling/computer system in accordance with the embodiments herein. The system comprises at least one processor or central processing unit (CPU) 10. The CPUs 10 are interconnected via system bus 12 to various devices such as a random access memory (RAM) 14, read-only memory (ROM) 16, and an input/output (I/O) adapter 18. The I/O adapter 18 can connect to peripheral devices, such as disk units 11 and tape drives 13, or other program storage devices that are readable by the system. The system can read the inventive instructions on the program storage devices and follow these instructions to execute the methodology of the embodiments herein. The system further includes a user interface adapter 19 that connects a keyboard 15, mouse 17, speaker 24, microphone 22, and/or other user interface devices such as a touch screen device (not shown) to the bus 12 to gather user input. Additionally, a communication adapter 20 connects the bus 12 to a data processing network 25, and a display adapter 21 connects the bus 12 to a display device 23 which may be embodied as an output device such as a monitor, printer, or transmitter, for example.

Figure 7:
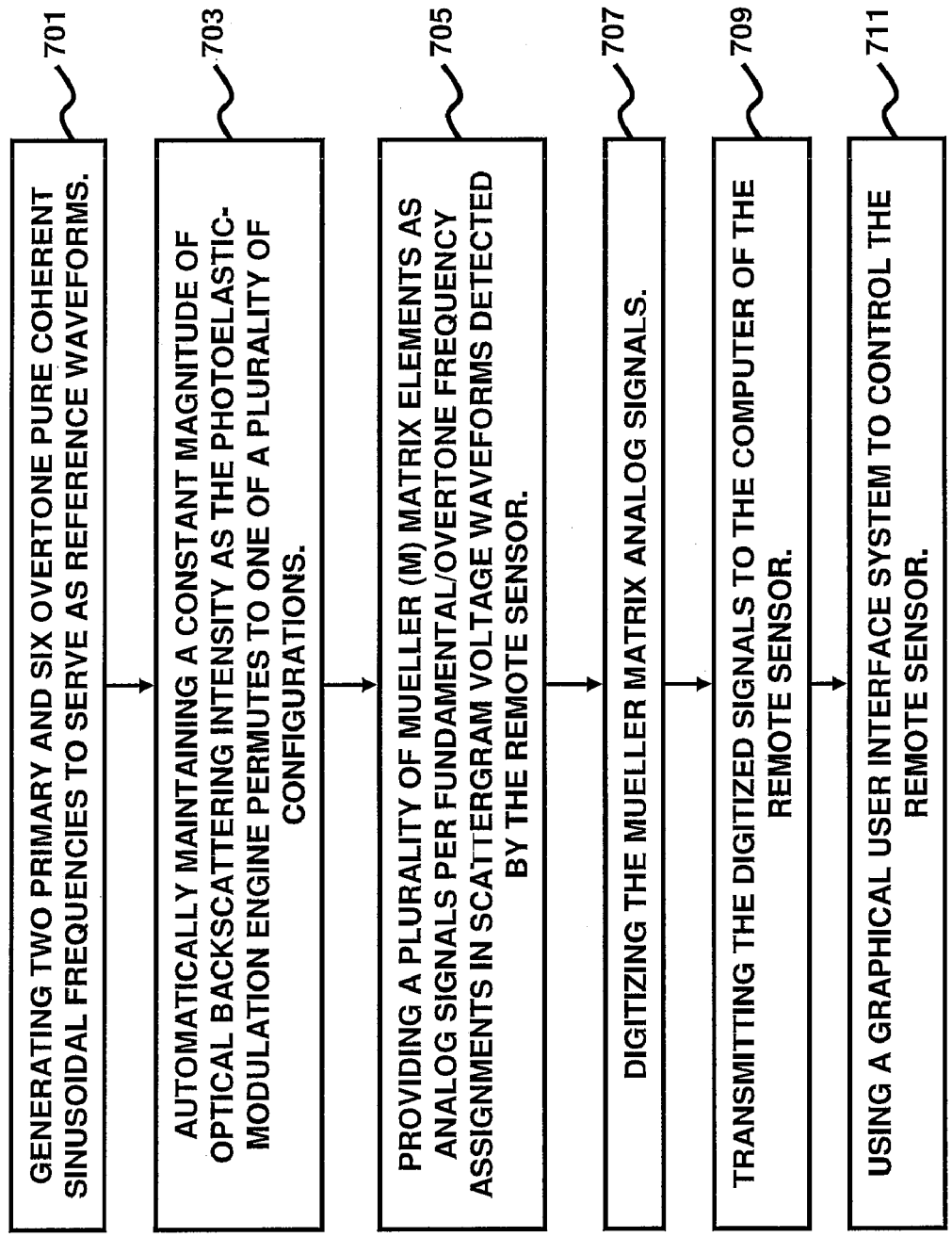
FIG. 7 is a flow diagram illustrating a method according to an embodiment herein.

FIG. 7, with reference to FIGS. 1 through 6, is a flow diagram illustrating a method of performing data acquisition using an electronics AMMS that receives data from an infrared photopolarimetric-based DIAMMS chemical and biological remote sensor 210 comprising a photoelastic-modulation engine and a computer 502 according to an embodiment herein, wherein the method comprises generating (701) two primary and six overtone pure coherent sinusoidal frequencies to serve as reference waveforms; automatically maintaining (703) a constant magnitude of optical backscattering intensity as the photoelastic-modulation engine permutes to one of a plurality of configurations; providing (705) a plurality of Mueller (M) matrix elements as analog signals per fundamental/overtone frequency assignments in scattergram voltage waveforms detected by the remote sensor 210; digitizing (707) the Mueller matrix analog signals; transmitting (709) the digitized signals to the computer 502 of the remote sensor 210; and using (711) a graphical user interface system to control the remote sensor 210. Preferably, the plurality of configurations comprises four configurations. Additionally, the plurality of Mueller (M) matrix elements comprises eight Mueller (M) matrix elements. Moreover, an output of the plurality of Mueller (M) matrix elements is proportional to a dot product between detected scattergram signals and each reference waveform. Moreover, the GUI system comprises automatic control of (i) an optical system 202 of the remote sensor 210, (ii) safety failsafe operations of the remote sensor 210, (iii) synchronized acquisition of Mueller matrix elements data, (iv) optimization of data measurements, and (v) preprocessing of acquired data and filtration of a database for susceptible difference-Mueller matrix elements. The method may further comprise developing neural network models (stored in CPU 502) using a database (stored in CPU 502) of Mueller matrix element; providing pattern recognition of chemical-biological analytes built from the database of Mueller matrix elements; and providing type-classification of analyte species built from the database of Mueller matrix elements.

The foregoing description of the specific embodiments will so fully reveal the general nature of the embodiments herein that others can, by applying current knowledge, readily modify and/or adapt for various applications such specific embodiments without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. Therefore, while the embodiments herein have been described in terms of preferred embodiments, those skilled in the art will recognize that the embodiments herein can be practiced with modification within the spirit and scope of the appended claims.

What is claimed is:

1. An electronics analog Mueller matrix system (AMMS) comprising:
    an infrared photopolarimetric-based differential-absorption Mueller matrix spectroscopy (DIAMMS) chemical and biological remote sensor comprising a photoelastic-modulation engine and a computer;
    a reference synthesizing module operatively connected to said remote sensor, said reference synthesizing module comprising circuits generating two primary and six overtone pure coherent sinusoidal frequencies to serve as reference waveforms;
    a scattergram intensity regulation and control module operatively connected to said reference synthesizing module, said scattergram intensity regulation and control module comprising an electromechanical system that automatically maintains constant magnitude of optical backscattering intensity as said photoelastic-modulation engine permutes to one of a plurality of configurations;
    a phase correlation module operatively connected to said scattergram intensity regulation and control module, wherein said phase correlation module provides a plurality of Mueller (M) matrix elements as analog signals per fundamental/overtone frequency assignments in scattergram voltage waveforms detected by said remote sensor;
    a data digitization and computer interface module operatively connected to said phase correlation module, wherein said data digitization and computer interface module digitizes the Mueller matrix analog signals from said phase correlation module and transmits the digitized signals to said computer of said remote sensor; and
    a graphical user interface (GUI) system operatively connected to said data digitization and computer interface module, wherein said GUI system controls said remote sensor.

2. The AMMS of claim 1, wherein said reference waveforms are input into junctions of phase-sensitive detection circuits of a succeeding phase correlation module of a second AMMS.

3. The AMMS of claim 1, wherein said plurality of configurations comprises four configurations.

4. The AMMS of claim 1, wherein said plurality of Mueller (M) matrix elements comprises eight Mueller, (M) matrix elements.

5. The AMMS of claim 1, wherein an output of said plurality of Mueller (M) matrix elements is proportional to a dot product between detected scattergram signals and each reference waveform transmitted by said reference synthesizing module.

6. The AMMS of claim 1, wherein said data digitization and computer interface module comprises a logic control circuit that controls sequences of command and status signals between said data digitization and computer interface module and said scattergram intensity regulation and control module.

7. The AMMS of claim 1, wherein said GUI system comprises automatic control of (i) an optical system of said remote sensor, (ii) safety failsafe operations of said remote sensor, (iii) synchronized acquisition of Mueller matrix elements data, (iv) optimization of data measurements, and (v) preprocessing of acquired data and filtration of a database for susceptible difference-Mueller matrix elements.

8. The AMMS of claim 1, further comprising:
a database of Mueller matrix elements to develop neural network models; and
a backward-error propagation neural network algorithm module that provides pattern recognition of chemical-biological analytes built from said database of Mueller matrix elements.

9. The AMMS of claim 8, further comprising:
a self-organization map neural network algorithm module that provides type-classification of analyte species built from said database of Mueller matrix elements.

10. A method of performing data acquisition using an electronics analog Mueller matrix system (AMMS) that receives data from an infrared photopolarimetric-based differential-absorption Mueller matrix spectroscopy (DI-AMMS) chemical and biological remote sensor comprising a photoelastic-modulation engine and a computer, said method comprising:
generating two primary and six overtone pure coherent sinusoidal frequencies to serve as reference waveforms;
automatically maintaining a constant magnitude of optical backscattering intensity as said photoelastic-modulation engine permutes to one of a plurality of configurations;
providing a plurality of Mueller (M) matrix elements as analog signals per fundamental/overtone frequency assignments in scattergram voltage waveforms detected by said remote sensor;
digitizing the Mueller matrix analog signals;
transmitting the digitized signals to said computer of said remote sensor; and
using a graphical user interface (GUI) system to control said remote sensor.

11. The method of claim 10, wherein said plurality of configurations comprises four configurations.

12. The method of claim 10, wherein said plurality of Mueller (M) matrix elements comprises eight Mueller (M) matrix elements.

13. The method of claim 10, wherein an output of said plurality of Mueller (M) matrix elements is proportional to a dot product between detected scattergram signals and each reference waveform.

14. The method of claim 10, wherein said GUI system comprises automatic control of (i) an optical system of said remote sensor, (ii) safety failsafe operations of said remote sensor, (iii) synchronized acquisition of Mueller matrix elements data, (iv) optimization of data measurements, and (v) preprocessing of acquired data and filtration of a database for susceptible difference-Mueller matrix elements.

15. The method of claim 10, further comprising:
developing neural network models using a database of Mueller matrix element;
providing pattern recognition of chemical-biological analytes built from said database of Mueller matrix elements; and
providing type-classification of analyte species built from said database of Mueller matrix elements.

16. An apparatus for performing data acquisition using an electronics analog Mueller matrix system (AMMS) that receives data from an infrared photopolarimetric-based differential-absorption Mueller matrix spectroscopy (DI-AMMS) chemical and biological remote sensor comprising a photoelastic-modulation engine and a computer, said apparatus comprising:
means for generating two primary and six overtone pure coherent sinusoidal frequencies to serve as reference waveforms;
means for automatically maintaining a constant magnitude of optical backscattering intensity as said photoelastic-modulation engine permutes to one of a plurality of configurations;
means for providing a plurality of Mueller (M) matrix elements as analog signals per fundamental/overtone frequency assignments in scattergram voltage waveforms detected by said remote sensor;
means for digitizing the Mueller matrix analog signals;
means for transmitting the digitized signals to said computer of said remote sensor; and
means for using a graphical user interface (GUI) system to control said remote sensor.

17. The AMMS of claim 16, wherein said plurality of configurations comprises four configurations.

18. The AMMS of claim 16, wherein said plurality of Mueller (M) matrix elements comprises eight Mueller (M) matrix elements.

19. The AMMS of claim 16, wherein an output of said plurality of Mueller (M) matrix elements is proportional to a dot product between detected scattergram signals and each reference waveform.

20. The AMMS of claim 16, wherein said GUI system comprises automatic control of (i) an optical system of said remote sensor, (ii) safety failsafe operations of said remote sensor, (iii) synchronized acquisition of Mueller matrix elements data, (iv) optimization of data measurements, and (v) preprocessing of acquired data and filtration of a database for susceptible difference-Mueller matrix elements.

21. The apparatus of claim 16, further comprising:
means for developing neural network models using a database of Mueller matrix element;
means for providing pattern recognition of chemical-biological analytes built from said database of Mueller matrix elements; and
means for providing type-classification of analyte species built from said database of Mueller matrix elements.

* * * * *